Feb. 12, 1957 R. A. BISBEE Plant Pat. 1,565
APPLE TREE
Filed May 3, 1956
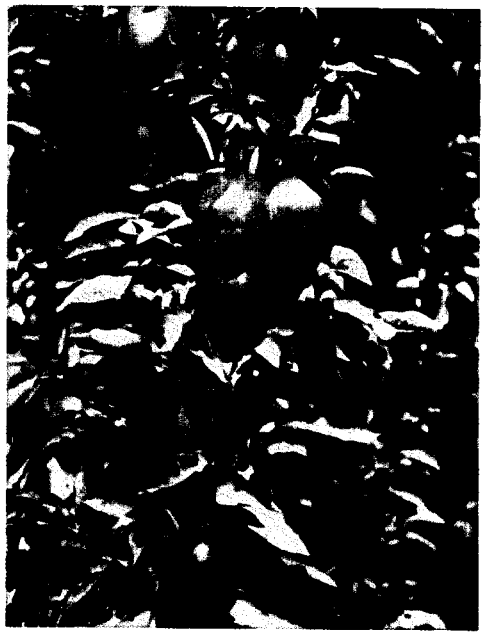
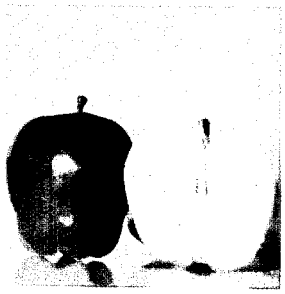
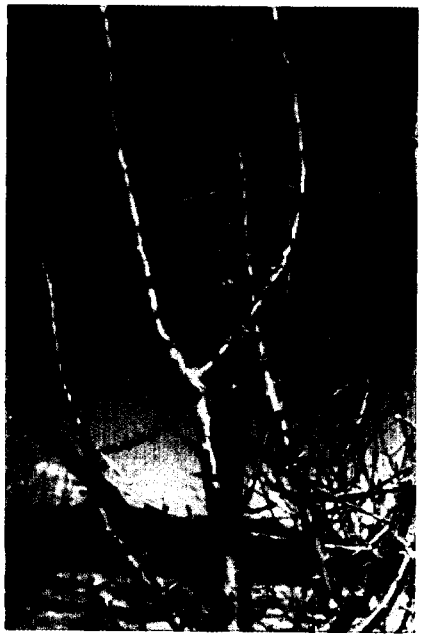
Inventor.
R. A. Bisbee
By: Robb & Robb
Attorneys.

United States Patent Office

Plant Pat. 1,565

Patented Feb. 12, 1957

1,565

APPLE TREE

Roy A. Bisbee, Hood River, Oreg., assignor to Stark Bro's Nurseries and Orchards Company, Louisiana, Mo., a corporation of Missouri Application May 3, 1956, Serial No. 582,613

1 Claim. (Cl. 47—62)

The present invention relates to a new and distinct variety of apple tree which was discovered by me as a bud sport of the variety which has long been sold in commerce under the trademark "Starking Delicious" (unpatented), the discovery having been made in my cultivated orchard which is located approximately four miles south of Hood River, Oregon.

At the time of my discovery, my attention was attracted to a particular tree in my orchard which appeared to be bearing fruit that was quite different from the normal fruit of the parent variety, such differences being evidenced by an earlier coloring of the fruit, as well as a color pattern in the form of a uniform over-all red blush that was quite different from the normal striped color pattern of the parent variety. Further and continued observations of the sport showed that its tree size was somewhat smaller than that of the trees of the parent variety of the same age, but more upright in growth, and the trees of the sport showed the development of considerably more fruit spurs than are normally found on trees of the parent variety. In addition, the new sport has proved to be earlier-bearing and highly productive at an earlier age than trees of the parent variety.

After my initial discovery of the sport, I promptly took steps to preserve and propagate the same, and asexual reproduction by grafting, as performed by me in my orchard near Hood River, Oregon, accompanied by continued observations and testing of the new sport, have fully established that the distinctive characteristics aforementioned come true to form and are established and transmissible through succeeding propagations.

While my new variety more nearly resembles its parent than any other variety, it is definitely distinguished therefrom, as well as from all other varieties of which I am aware, and the distinctive features thereof constitute substantial improvements over the parent variety and represent exceedingly desirable characteristics from both a commercial and home orchard stand-point.

The accompanying drawing shows typical specimens of the foliage and fruit of my new variety, as well as the fruiting spur growth of a typical tree thereof, all as depicted in color as nearly true as it is reasonably possible to make the same in a color illustration of this character, with one of the views of the drawing showing a cross-section of a typical fruit specimen.

The following is a detailed description of my new variety, with color terminology in accordance with Ridgway's Color Standards and Nomenclature, and with the Horticultural Color Guide, as indicated, except where general color terms of ordinary dictionary significance are obvious:

Observations made from specimens grown near Hood River, Oregon.

Dates first and last pickings: From about September 25th to about October 10th; usually ripens simultaneously with the trademarked variety "Starking Delicious."

Tree: Medium size; medium vigorous; upright; dense;

vase-formed; hardy; very productive; regular bearing.

*Trunk.*—Medium stocky; medium smoothness.

*Branches.*—Medium thickness; smooth; with many spurs. Twigs—color — Diamine Brown, Plate XIII, Color No. 3′, Tone M (Ridgway). Lenticels—medium number; medium size.

*Leaves.*—Medium size; medium width (about 2⅛ inches); medium length (about 3½ inches); ovate; taper-pointed; thick; rugose. Color—Ivy Green, Plate 0960, p. 187, vol. 2 (Horticultural Color Guide). Margin—coarsely serrate. Petiole—medium length (about 1 inch); thick.

Flowers: Medium early; large.

*Color.*—White, with tinge of Carmine, Plate 21/3, p. 21, vol. 1 (Horticultural Color Guide).

*Date of first bloom.*—May 11th.

*Date of full bloom.*—May 15th.

Fruit:

*Maturity when described.*—Eating ripe.

*Size.*—Uniform. Axial diameter—about 3½ inches. Transverse diameter—about 3⅛ inches.

*Shape.*—Conical; ribbed.

*Cavity.*—Symmetrical; rounded toward apex; acute; undulate; pubescent toward apex. Depth—about ½ inch. Breadth—about 1¼ inches.

*Markings.*—Some present near apex. Color—Wood Brown, Plate XL, Color No. 17‴ (Ridgway).

*Basin.*—Symmetrical; flaring base; wide; furrowed; mammiform. Depth—about ⅜ inch. Breadth—about 1 1/16 inches.

*Stem.*—Clubbed; stout; pubescent; about ⅞ inch long.

*Calyx.*—Closed; segments persistent; broadly lanceolate; acute; about 5/16 inch long; approximate at base; prostrate; reflexed from base at apex. Outer surface—pubescent. Inner surface—pubescent.

*Eye.*—Small; partially closed.

*Skin.*—Thick; tough; smooth; waxed. Dots—obscure; few; small; even; ruptured; angular; color—Chinese Yellow, Plate 606/3, p. 68, vol. 1 (Horticultural Color Guide); distribution—uniform. Ground color—Straw Yellow, Plate 604/1, p. 67, vol. 1 (Horticultural Color Guide). Color markings—blushed; self-colored; bright; color—Chrysanthemum Crimson, Plate 842/2, p. 169, Vol. 2 (Horticultural Color Guide).

*Bloom.*—Wanting.

*Scarfskin.*—Wanting.

*General color effect.*—Deep red all over.

*Flesh.*—Rather juicy. Color—Satiny White, with Yellowish tint and tinged with Carmine, Plate 21, p. 21, vol. 1 (Horticultural Color Guide) in vascular bundles. Texture—firm; fine; crisp. Flavor—mild; rich. Aroma—distinct. Quality—best.

*Core.*—Median; distinct in cross-section; indistinct carpellary area. Bundle area—medium size; cordate; symmetrical at base; acute at base; in bundles opposite and alternate with cell. Halves of core—unequal. Bundles—inconspicuous; in one whorl; color—Chartreuse Green, Plate 663/3, p. 90, vol. 1 (Horticultural Color Guide). Core lines—clasping. Calyx tube—glabrous toward base; broadly obconic; urn-shaped; depth of tube to shoulder about 3/16 inch; entire depth about 9/16 inch. Styles—present; distinct toward base; pubescent toward base. Stamens—in one distinct whorl; marginal. Axillary cavity—present. Seed cells—axile; open. Cell walls—distant; thick; tough; length—about ⅝ inch; breadth—about 5/16 inch. Longitudinal section—broadly oval; acute at apex. Cross section—broad. Surface—fissured.

Seeds:

*Number.*—5 perfect; 3 imperfect; 2 per cell. Length—about 5/16 inch. Breadth—about 5/32 inch.

*Form.*—Obtuse.

*Color.*—Chestnut, Plate II, Color No. 9, Tone *m* (Ridgway).

Use: Market; dessert.

Keeping quality: Good; about 110 days in ordinary storage.

I claim:

A new and distinct variety of apple tree, substantially as herein shown and described, characterized particularly as to novelty by its general similarity to the trademarked variety "Starking Delicious" (unpatented), but being distinguished therefrom by its somewhat smaller tree size but more upright growth, its development of more fruit spurs, its earlier-bearing habit and greater productivity, the earlier coloring of its fruit, and the more uniform over-all red blush of its fruit.

No references cited.